United States Patent [19]

Nelson et al.

[11] Patent Number: 5,252,463
[45] Date of Patent: Oct. 12, 1993

[54] CLIPSIN, A CHYMOTRYPSIN-LIKE PROTEASE AND METHOD OF USING SAME

[75] Inventors: Robert B. Nelson, No. Chelmsford, Mass.; Robert G. Siman, Wilmington, Del.

[73] Assignee: The Du Pont Merck Pharmaceutical Company, Wilmington, Del.

[21] Appl. No.: 543,618

[22] Filed: Jun. 22, 1990

[51] Int. Cl.$^5$ ............................................. C12Q 1/37
[52] U.S. Cl. .......................................... 435/23; 435/4; 435/184; 435/212; 424/94.64
[58] Field of Search ...................... 435/4, 23, 184, 212; 424/94.64

[56] References Cited

U.S. PATENT DOCUMENTS

| | | | |
|---|---|---|---|
| 4,499,082 | 2/1985 | Shenvi et al. | 514/2 |
| 4,596,822 | 6/1986 | Powers et al. | 435/184 |
| 4,666,829 | 5/1987 | Glenner et al. | |
| 4,919,915 | 4/1990 | Averback | 436/164 |

FOREIGN PATENT DOCUMENTS 88108817 12/1988 European Pat. Off. .
9113904 9/1991 PCT Int'l Appl. .

OTHER PUBLICATIONS

Abraham et al. "Proteolytic Processing of β-Protein Precursor-Related Synthetic Peptides" Soc of Neuroscience Abstracts 15(1) 1989. [BIOSIS]
Festoff, B. "Zeroing in on Amyloid Proteins in Alzheimer's Disease Therapy" Neurobiology of Aging, vol. 10, pp. 466.
Soreq, et al. Dev Brain Res 11(2) 1983 pp. 149–158 "Plasminogen Activator in the Developing Rat Cerebellum . . . " [BIOSIS Abstract]
Bowen et al. "Cathepsin A in Human Brain and Spleen" J. Biochem (1973) 131 pp. 417–418.
Weber et al, "The Reliabiliy of Molecular Weight Determinations by DDS-PAGE" J. Proc. Chem. (1969) V 224 No. 16 pp. 4406–4412.
Abraham et al "A Calcium-Activated Protease from Alzheimer's Disease . . . " Biochem and Biophys Res. Comm 174(2) 1991 pp. 790–796.
Siman et al. "Proteolytic Processing of βamyloid precursor by calpain I" J. Neuroscience 10(7) 1990 pp. 2400–2411. (Jul. 1990).
*Enzyme Nomenclature* 1984 Academic Press NYC. International Union of Biochemistry pp. 346, 348.
Virca et al, (1984) Eur. J. Biochem. 144, 1–9.
Beatty et al, (1980) J. Biol. Chem. 255, 3931–3934.
Kettner et al, (1984) J. Biol. Chem. 259, 15106–15114.
Justice et al, (1987) J. Cell Biochem. 34, 227–238.
Abraham et al, (1990) Neurobiol. Aging, 10: 463–465.
Allsop et al, (1983) Brain Res. 259, 348–352.
Glenner et al, (1984) Biochem. Biophys. Res. Commun. 122, 1131–1135.
Kang et al, (1987) Nature 325, 733–736.
Card et al, (1988) Neuron 1, 835–846.
Kitaguchi et al, (1988) Nature 331, 530–532.
Ponte et al, (1988) Nature 331, 525–527.
Tanzi et al, (1988) Nature 331, 528–530.
Siman et al, (1989) Neuron 3, 275–285.

(List continued on next page.)

*Primary Examiner*—Michael G. Wityshyn
*Assistant Examiner*—T. J. Reardon
*Attorney, Agent, or Firm*—Blair Q. Ferguson

[57] ABSTRACT

A novel $M_r$ 25,000 chymotrypsin-like protease, termed clipsin, which binds to a-1-AChy in a sodium dodecyl sulfate-resistant manner, preferentially degrades β-APP, and shows high activity for a period of a few days in neonatal rat brain is disclosed. Preparation of clipsin in a form that allows clipsin proteolytic activity to be measured under conditions substantially free of the activity other cellular non-clipsin proteases is also disclosed. Further disclosed is a method of identifying potential therapeutic agents for the treatment of selected neuropathologies such as Down's syndrome and Alzheimer's disease by measuring or inhibition of clipsin.

5 Claims, No Drawings

OTHER PUBLICATIONS

Heussen et al, (1980) Anal. Biochem. 102, 196–202.
Miskin et al, (1981) Anal. Biochem. 118, 252–258.
Travis et al, (1978) Biochemistry 17, 5651–5656.
Azaryan et al., Neurochemical Research 14:995–1001 (1989).
Wilk and Orlowski, J. Neurochemistry 40:842–849 (1983).
Abraham, Neurobiology of Aging 10:463–465 (1989).
Nelson and Siman, J. Neurochemistry 53:641–647 (1989).
Ibrahim, Acta Anat. 124:149–158 (1985).
Nelson and Siman, J. Biol. Chem. 265:3836–3843 (Mar. 1990).
Carrell, Nature 331:478–479 (1988).
Cataldo and Nixon, Proc. Natl. Acad. Sci. USA 87:3861–3865 (May 1990).
Barrett, Methods in Enzymology 80:561–565 (1981).
Woodbury et al., Methods in Enzymology 80:588–609 (1981).
Kato et al., J. Biochem. 103:820–822 (1988).
Nakajima et al., J. Biol. Chem. 254:4027–4032 (1979).
Marx, Science 243:1664–1666 (1989).
Abraham et al., Cell 52:487–501 (1988).
Abraham and Potter, Biotechnology 7:147–153 (1989).
Powers and Harper, Proteinase Inhibitors pp. 55–152 (1986).
Abraham and Potter, Society for Neuroscience Abstracts 15:648 (Nov. 1989).
Nelson and Siman, Society for Neuroscience Abstracts 15:330 (Nov. 1989).

CLIPSIN, A CHYMOTRYPSIN-LIKE PROTEASE AND METHOD OF USING SAME

FIELD OF INVENTION

This invention relates to a novel protease, refered to as clipsin, and to methods of using same to obtain and use compounds in treating selected neuropathologies such as Alzheimer's disease and Down's syndrome.

BACKGROUND OF THE INVENTION

There are a number of serious diseases affecting the central nervous system. These diseases, referred to as neuropathologies, include Down's syndrome and Alzheimer's disease. Down's syndrome is a congenital condition involving moderate to severe mental deficiency. Alzheimer's Disease is a form of dementia marked by progressive intellectual deterioration without focal, motor or sensory signs. It is an insidious, progressive, debilating disease of unknown etiology afflicting almost two million Americans, most of them elderly.

Although the etiology of Alzheimer's disease is unknown, researchers have identified three histopathological structures which are present in the brains of Alzheimer's patients: neurofibrillary tangles, neuritic (senile) plaques, and cerebrovasculature plaques. Neurofibrillary tangles are intracellular accumulations of fibrous material in the cell bodies of affected neurons, mainly in the hippocampus, amygdala and neocortex. Neuritic and cerebrovascular plaques are found in highest concentration in the hippocampus and neocortex and result from a pathological deposition of amyloid precursor protein(s) (APP) or fragments thereof in these regions, such as described in U.S. Pat. No. 4,666,829, incorporated herein by reference. It should be noted that the term amyloid, as used in a neuropathological context, refers to the deposition of APP and its fragments into plaques. This differs from the usage of the term in the general, histopathological context. Specifically, when applied to neuropathological plaques, the term most commonly refers to the A4 amino acid fragment of APP. In standard histopathological uses the term amyloid refers to a refractive, insoluble, noncellular material.

It appears that protease inhibitor systems may participate in certain neuropathologies. In both Down's syndrome and Alzheimer's disease, an insoluble peptide termed β-amyloid aggregates into neuritic plaques (Allsop et al., (1983) Brain Res. 259, 348-352; Glenner et al., (1984) Biochem. Biophys. Res. Commun. 122, 1131-1135 Masters et al., (1985) Proc. Nat'l. Acad. Sci. U.S.A. 82, 4245-4249; Castan et al., (1986) Biochem. Biophys. Res. Commun. 141, 782-789; Kirschner et al., (1987) Proc. Nat'l. Acad. Sci. U.S.A. 84, 6953-6957). β-Amyloid is derived from one or more β-amyloid precursor proteins (β-APP) (Kang et al., (1987) Nature 325, 733-736; Kitaguchi et al., (1988) Nature 331, 530-532; Ponte et al., (1988) Nature 331, 525-527; Tanzi et al., (1988) Nature 331, 528-530), which are normal neuronal constituents (Card et al., (1988) Neuron 1, 835-846). The generation of β-amyloid appears to result from inappropriate processing of β-APP by one or more proteases (Glenner et al., (1987) in Banbury Report 27: Molecular Neuropathology of Aging (Davies, P., and Finch, C. E., eds) pp. 253-255, Cold Spring Harbor Laboratory, Cold Spring Harbor, N.Y.; Kang et al., (1987) Nature 325, 733-736; Grundke-Iqbal et al., (1989) Proc. Nat'l. Acad. Sci. U.S.A. 86, 2853-2857; Weidemann et al., (1989) Cell 57, 115-126). Specifically, the amino terminus of β-amyloid is formed through hydrolysis of βAPP on the carboxyl side of methionine$^{596}$ (Kang et al., (1987) Nature 325, 733-736). Based upon the affinities of known proteases for primary protein structure, such a cleavage event is predicted to result through the action of a chymotrypsin-like enzyme (Barrett et al., (1980) Mammalian Proteases, Vol. 1, Academic Press, New York; Lorand (1981) Methods Enzymol 80, 1-919).

β-Amyloid is one of two identified integral components of neuritic plaques. The second known component is α-1-antichymotrypsin (α-1-AChy) (Abraham et al., (1988) Cell 52, 487-501), a protease inhibitor that forms sodium dodecyl sulfate-resistant bonds with chymotrypsin-like enzymes (Travis et al., (1978) Biochemistry 17, 5651-5656). It is not yet known whether α-1-AChy might be associated with neuritic plaques by virtue of its binding to a chymotrypsin-like protease which itself is an integral plaque component. α-1-AChy has also been reported in normal brain (Justice et al., (1987) J. Cell. Biochem 34, 227-238; Abraham et al., (1990) Neurobiol Aging, in press).

SUMMARY OF THE INVENTION

This invention features substantially pure clipsin, a novel protease which we have prepared in a form that allows clipsin proteolytic activity to be measured under conditions substantially free of the activity of other cellular non-clipsin proteases. This invention also features a method of identifying therapeutic agents for the treatment of selected neuropathologies such as Down's syndrome and Alzheimer's disease by measuring inhibition of clipsin.

Clipsin is a novel $M_r$ 25,000 α-1-antichymotrypsin-binding protein classified as a chymotrypsin-like protease by its inhibitor profile and substrate specificity. Release of $^{125}$I-labeled breakdown products from bands containing clipsin in substrate-linked polyacrylamide gels (enzymography) was examined in parallel with hydrolysis of tetrapeptide chromogenic substrates in vitro to establish conditions under which clipsin was the only activity being measured in vitro.

Clipsin is completely membrane-associated but is extractable using 1M MgCl$_2$; prior extraction of detergent-soluble and low ionic strength-soluble proteins from membranes increases its specific activity. Clipsin is surprisingly resistant to solubilization by detergent. The formation of sodium dodecyl sulfate-resistant bonds between human α-1-antichymotrypsin and clipsin ($k_{assoc}=2.9\times10^6M^{-1}s^{-1}$) is usable to titrate the concentration of free protease solubilized from membranes. Clipsin cleaves both succinyl-Ala-Ala-Pro-Phe-p-nitroanilide and methoxy-succinyl-Ala-Ala-Pro-Met-p-nitroanilide, the latter being of interest because cleavage after a methionine residue appears to generate the amino terminus of the neuritic plaque component β-amyloid from its precursor protein. Solubilized clipsin degraded 90% of membrane-associated β-amyloid precursor protein detected by Western blot analysis.

Clipsin is kinetically distinct from both chymotrypsin and cathepsin G and does not match kinetic values published for the rat mast cell proteases against comparable substrates. Proteases similar to and potentially identical to clipsin are detected by enzymography in rat brain and in other organs from rat (most notably spleen and adult lung). The enzyme in brain was distinguished by a narrow window of elevated activity surrounding postnatal day 5, which was 12–14-fold higher than levels in day 1 or adult brain. We believe that the brain chymotrypsin-like protease clipsin is involved in the etiology of Down's syndrome and Alzheimer's disease.

DETAILED DESCRIPTION OF THE INVENTION

We have discovered a novel $M_r$ 25,000 protease in rat brain which we have designated "clipsin". Clipsin was inhibited by the general serine protease inhibitors phenylmethylsulfonyl fluoride and diisopropyl fluorophosphate and not by inhibitors specific for the other three classes of protease. Within the serine class, clipsin was preferentially inhibited by MeO-Suc-Ala-Ala-Pro-boro-Phe, which is specific for chymotrypsin-like proteases (Kettner et al., (1984) *J. Biol. Chem.* 259, 15106–15114; U.S. Pat. No. 4,499,082, issued Feb. 12, 1985), incorporated herein by reference. As disclosed in the '082 patent, the compounds where R2 is Tyr, Trp, Phe, Met, or Leu are inhibitors of chymtrypsin-like proteases. Clipsin selectively hydrolyzed Suc-Ala-Ala-Pro-Phe-p-nitroanilide and MeO-Suc-Ala-Ala-Pro-Met-p-nitroanilide, two prototypical synthetic substrates of chymotrypsin-like proteases but could be distinguished from pancreatic and leukocyte elastase through its lack of inhibition by MeO-Suc-Ala-Ala-Pro-boro-Ala-OH and MeO-Suc-Ala-Ala-Pro-boro-Val-OH, respectively, (Kettner et al., (1984) J. Biol. Chem. 259, 15106–15114) and its inability to hydrolyze the two p-nitroanilide counterparts of these tetrapeptides. Clipsin exhibits the specificity of a chymotrypsin-like protease, that is, the protease is selective for peptide bonds on carboxyl side of the aromatic side chains tyrosine tryptophan, and phenylalanine and the large hydrophobic residues, such as methionine or leucine. Chymotripsin-like proteases also hydrolyze ester bonds.

Both enzymography and an in vitro chromogenic substrate assay were used in parallel to characterize chromotrypsin-like activity in the clipsin-enriched $Mg^{2+}$ extract, as described below. This approach allowed us to establish conditions under which clipsin activity as detected by enzymography was the only protease activity measured in vitro. Although it is possible that there is more than one chymotrypsin-like protease in the $Mg^{2+}$ extract, this is argued against by: (a) the lack of any other protease activities on the enzymographs under the conditions used to assay clipsin; (b) the co-titration using $\alpha$-1-AChy of chymotrypsin-like activity in vitro and clipsin activity on enzymographs; (c) the parallel ontogeny of brain chymotrypsin-like activity in vitro with the ontogeny of clipsin activity on enzymographs; and (d) the tight correspondence of in vitro and enzymographic inhibitor profiles. Clipsin also appears to be quite stable in $Mg^{2+}$ extract as indicated by its linear substrate hydrolysis over 90 min or more in vitro.

Among chymotrypsin-like enzymes, clipsin could be kinetically distinguished from both chymotrypsin and cathepsin G. Clipsin resembled cathepsin G in terms of its greater relative affinity for the methionine-versus phenylalanine-containing p-nitroanilide substrate; however, clipsin had an 11-fold greater catalytic efficiency against Suc-Ala-Ala-Pro-Phe-p-nitroanilide than MeO-Suc-Ala-Ala-Pro-Met-p-nitroanilide, whereas cathepsin G was equally reactive against the two substrates. It is unlikely that the kinetic differences between cathepsin G and clipsin were related to species differences in the enzyme because human and rat leukocyte cathepsin G have been reported to exhibit similar kinetic profiles (Virca et al., (1984) *Eur. J. BioChem.* 144, 1–9). Chymotrypsin was quite distinct kinetically from clipsin, having $k_{cat}/K_m$ values 8.5-fold and 16-fold greater than clipsin for MeO-Suc-Ala-Ala-Pro-Met-p-nitroanilide and Suc-Ala-Ala-Pro-Phe-p-nitroanilide, respectively.

Clipsin was shown further to be a chymotrypsin-like enzyme in its property of binding to $\alpha$-1-AChy in a sodium dodecyl sulfate-resistant manner. Our determination of clipsin's binding affinity for $\alpha$-1-AChy ($k_{assoc}=2.9\times10^6 M^{-1}s^{-1}$) is close to 2 orders of magnitude higher than the $k_{assoc}$ reported for $\alpha$-1-AChy binding to bovine chymotrypsin ($6.0\times10^4 M^{-1}s^{-1}$) but is about 1 order of magnitude lower than that reported for human cathepsin G ($5.1\times10^7 M^{-1}s^{-1}$; Beatty et al., (1980) *J. Biol. Chem.* 255, 3931–3934). The demonstration that $\alpha$-1-AChy stably binds to clipsin, aside from allowing the titration of enzyme present in our clipsin-enriched extract, also was important in that $\alpha$-1-AChy or an $\alpha$-1-AChy-like protein has been found in the normal human central nervous system (Justice et al., (1987) *J. Cell. Biochem.* 34, 227–238; Abraham et al., (1990) *Neurobiol. Aging, in press*).

Brain $\alpha$-1-AChy has received increasing attention due to its identification as an integral component of neuritic plaques in Down's syndrome and Alzheimer's disease (Abraham et al., (1988) *Cell* 52, 487–501). Isolation of neuritic plaques includes sodium dodecyl sulfate treatment to remove loosely associated proteins; however, the ability of $\alpha$-1-AChy to form sodium dodecyl sulfate-resistant bonds with its target proteases invites the question as to whether a chymotrypsin-like protease with $\alpha$-1-AChy bound to it might also be an integral plaque component.

A second line of evidence suggesting involvement of chymotrypsin-like enzymes in neuritic plaque formation lies in the generation of $\alpha$-amyloid—the first identified neuritic plaque component—from the normal brain protein $\beta$-APP (Allsop et al., (1983) *Brain Res.* 259, 348–352; Glenner et al., (1984) *Biochem. Biophys. Res. Commun.* 122, 1131–1135; Kang et al., (1987) *Nature* 325, 733–736; Card et al., (1988) *Neuron* 1, 835–846; Kitaguchi et al., (1988) *Nature* 331, 530–532; Ponte et al., (1988) *Nature* 331, 525–527; Tanzi et al., (1988) *Nature* 331, 528–530). The amino terminus in $\beta$-amyloid results from hydrolysis at the carboxyl end of methionine residue 596 (Kang et at., (1987) *Nature* 325, 733–736). Such a cleavage event has been demonstrated at physiologically relevant rates only for the chymotrypsin-like proteases (Barrett et al., (1980) *Mammalian Proteases, Vol. 1, Academic Press, New York*; Lorand, L. (1981) *Methods Enzymol.* 80, 1–919), although such studies consider only primary protein structure. As a first step in determining potential endogenous substrates for clipsin, we tested the ability of clipsin to degrade major Coomassie Blue-detectable proteins from rat cortical membranes and, in parallel, examined degradation of $\beta$-APP from this same source using a carboxyl-terminal-directed antibody. $\beta$-APP proved to be an excellent substrate for clipsin, although the site(s) of cleavage are not proven.

Materials used in the following Examples were obtained as follows. Bovine $\alpha$-chymotrypsin treated with 1-chloro-3-tosylamido-7-amino-2-heptanone, human leukocyte cathepsin G, MeO-Suc-Ala-Ala-Pro-Phe-p-nitroanilide, and Suc-Ala-Ala-Met-p-nitroanilide were obtained from Sigma. Human $\alpha$-1-AChy was from Calbiochem. MeO-Suc-Ala-Ala-Pro-boro-Phe-OH , MeO-Suc-Ala-Ala-Pro-boro-Ala-OH, MeO-Suc-Ala-Ala- Pro-boro-Val-OH, (U.S. Pat. No. 4,499,082 to Kettner and Shenvi, issued Feb. 12, 1985), and Bz-Pro-Phe-boro-Arg-OH (European Patent Application Number 88108817.3, to Kettner and Shenvi, published Dec. 7, 1988) were supplied by Dr. Charles Kettner, Du Pont Experimental Station, Wilmington, Del. Antiserum 385, raised against a synthetic peptide corresponding to residues 676–695 of β-APP (numbering according to Kang et al., (1987) Nature 325, 733–736), was prepared and characterized as described previously (Card et al., (1988) Neuron 1, 835–846; Siman et al., (1989) Neuron 3, 275–285).

All procedures for preparing Clipsin extract were performed at 4° C. unless otherwise indicated. Forebrains from 5-day-old rats were stripped of meninges and homogenized in 20 volumes of 50 mM Hepes (pH 7.5), 1 mM EDTA, and 1% Triton X-100 (or 1% CHAPS). The homogenate was allowed to remain for 30 min with occasional vortexing and was then centrifuged 1 h at 40,000 rpm (150,000×$g_{avg}$) in a Sorvall 50.38 rotor. For the low ionic strength extraction, the pellet was resuspended to original volume in 1 mM Hepes (pH 7.5), 0.1 mM EDTA, made up in 18 megaohm resistance water that had been passed through a chelating resin column (Chelex ® 100). The resuspension was shaken in a water bath for 1 h at 37° C. and then centrifuged as above. Pellets were resuspended to 10% original volume in 50 mM Hepes (pH 7.5), 1M $MgCl_2$, and 0.1% Brij 35, and allowed to remain on ice for 30 min with occasional vortexing. Samples were centrifuged as above for 1 h. The supernatant from this extraction was dialyzed exhaustively against 20 mM Hepes (pH 7.5), 0.5M NaCl, 1 mM EDTA, and 0.1% Brij 35. The resulting $Mg^{2+}$ extract could be frozen with no appreciable loss of activity and was stored at −80° C. for subsequent use in the in vitro assay described below.

For the ontogeny and tissue distribution studies, in which $Mg^{2+}$ extracts were prepared on a small scale from multiple sources, the procedure was identical to that above except that centrifugation was carried out in a tabletop ultracentrifuge using a TLA-100.2 Beckman rotor. Each centrifuge run was for 20 min at 80,000 rpm (350,000×$g_{avg}$). For the tissue distribution study, both the 5-day-old rats and adult rats were deeply anesthetized with Pseudochlor (1 mg/kg) prior to being perfused intracardially with ice-cold phosphate-buffered saline. This removed blood cells and serum as contributors to the protease complement detected in the various organs. Following the perfusion, tissues were dissected out on ice, minced, sonicated in the detergent-containing buffer (see above), and processed for $Mg^{2+}$ extract preparation. Final protein concentration of each $Mg^{2+}$ extract was adjusted using the method of Bradford (1976).

Enzymography was conducted by assaying Protease activity in $^{125}$I-gelatin-containing polyacrylamide gels as described previously (Nelson et al., (1989) J. Neurochem. 53, 641–647). Following removal of sodium dodecyl sulfate from the gels and incubation of the gels in conditions favoring reactivation of protease-containing bands, gelatinolytic activity is detected through electrophoretic transfer of $^{125}$I-labeled breakdown products onto nitrocellulose paper, followed by autoradiography. A variety of proteases has been shown to retain activity using this type of assay (Heussen et al., (1980) Anal. Biochem. 102, 196–202; Miskin et al., (1981) Anal. Biochem. 118, 252–258; Nelson et al., (1989) J. Neurochem. 53, 641–647). The effects of inhibitors on electrophoretically separated proteases were tested by preequilibrating the gelatin-containing polyacrylamide gel strips in inhibitor-containing buffers for 20 min at 4° C. prior to activating proteases by incubation of the gels in a humidified chamber at 37° C.

The hydrolysis rates of several tetrapeptide p-nitroanilides by clipsin and other chymotrypsin-like proteases were measured by incubating 180 μL of enzyme in $Mg^{2+}$ extract buffer with 20 μL of p-nitroanilide substrate in dimethyl sulfoxide. Reactions were usually carried out for 60 min and then stopped by the addition of 100 μL of 200 μg/mL soybean trypsin inhibitor. In pilot studies, we determined that the chymotrypsin-like enzymes, including clipsin, were stable at 50° C., as reported previously for chymotrypsin-like enzymes (Barrett, A. J. (1981) Methods Enzymol. 80, 561–565); therefore, kinetic studies were run at this temperature to increase the reaction rate. Using Suc-Ala-Ala-Pro-Phe-p-nitroanilide as substrate, we also adjusted the concentrations of chymotrypsin and cathepsin G to obtain reaction rates approximately equal to that of a 5-fold dilution of $Mg^{2+}$ extract. Under these conditions, substrate hydrolysis was linear for at least 90 min. The increase in absorbance at 405 nm was measured using an Artek microtiter plate reader and converted to concentration of nitroaniline generated using an ε of $1.07 \times 10^4 M^{-1} cm^{-1}$ (Virca et al., (1984) Eur. J. Biochem. 144, 1–9). The kinetic constants were determined from initial rates of hydrolysis by the Lineweaver-Burk method and are based on triplicate determinations at five or six separate substrate concentrations chosen so that values of reciprocal concentrations would be evenly proportioned. Correlation coefficients were greater than 0.99.

In cases in which boronic acid peptide inhibitors or α-1-AChy were tested in vitro, 160 μL of enzyme in $Mg^{2+}$ extract buffer was preincubated with 20 μL of inhibitor in $Mg^{2+}$ extract buffer for 20 min at 37° C. before addition of 20 μL of substrate solution in dimethyl sulfoxide for 1 h and termination with 100 μL of 200 μg/mL soybean trypsin inhibitor.

α-1-AChy produces a progressive time-dependent inhibition due to its formation of sodium dodecyl sulfate-resistant complexes with its substrates (Travis et al., (1978) Biochemistry 17, 5651–5656). After determining that concentrations of α-1-AChy of about 3.5 nM or higher produced rapid inhibition of clipsin activity in 20% $Mg^{2+}$ extract, we explored the time course of complete association using lower α-1-AChy concentrations. 20% $Mg^{2+}$ extract was incubated with a range of α-1-AChy concentrations in $Mg^{2+}$ extract buffer at 37° C. After fixed intervals, 180 μL aliquots were removed and mixed with 20 μL of substrate solution (2 mM final) and then incubated at 50° C. for 1 h before terminating the reaction with 100 μL of 200 μg/mL soybean trypsin inhibitor. Initial velocities in the presence of inhibitor were compared with the control (no α-1-AChy), and percent activities were calculated. At all time points, linear inhibition curves were obtained allowing the determination of a titration point for clipsin using the inhibitor (Beatty et al., (1980) J. Biol. Chem. 255, 3931–3934; Kettner et al., (1984) J. Bio. Chem. 259, 15106–15114). We then graphed these titration points with respect to time to determine when α-1-AChy inhibition of clipsin approached completion. The asymptotic titration value was provisionally used as the titrated concentration of clipsin in $Mg^{2+}$ extract. Verification that this binding was rapid and irreversible was through determination of the association rate constant (see below) and through the demonstration on enzymographic gels that this binding was stable in the presence of sodium dodecyl sulfate.

The association rate constant for $\alpha$-1-AChy binding to clipsin was determined under second-order conditions as described previously for $\alpha$-1-AChy binding to other chymotrypsin-like proteases (Beatty et al., (1980) *J. Biol. Chem.* 255, 3931-3934). Using the titrated concentration of clipsin, an equimolar concentration of $\alpha$-1-AChy was preincubated with $Mg^{2+}$ extract for various periods of time before addition of 2 mM substrate which stopped the reaction and was used to measure residual enzyme activity. The half-life time of reaction ($t_{\frac{1}{2}}$) was calculated from a plot of $v^{-1}$ versus t, and in turn used to calculate the association rate constant $k_{assoc}$ through the following: $k_{assoc}=1/t_{\frac{1}{2}}[E\gamma]$, where $[E\gamma]$ stands for the total enzyme concentration (Beatty et al., (1980) *J. Biol. Chem.* 255, 3931-3934).

$Mg^{2+}$ extract at 60% (about 4.2 nM clipsin final) was incubated with a crude membrane fraction from adult rat cortex (2.8 mg/mL protein final; Siman et al., (1989) *J. Neurosci.* 9, 1579-1590). Proteolysis reactions were performed at 37° C. for 1 h before quenching the reactions with sodium dodecyl sulfate-containing electrophoresis sample buffer and heating the samples to 90° C. for 5 min. Overall breakdown of proteins were determined by Coomassie Blue staining of gels, whereas $\beta$-APP degradation was assessed by Western blotting of identical gels. $\beta$-APP was visualized as 110-130-kDa bands using antiserum 385 as described previously (Siman et al., (1989) *Neuron* 3, 275-285). $\beta$-APP-immunostained polypeptides on Western blots and the corresponding major Coomassie Blue-stained protein bands on sodium dodecyl sulfate-containing polyacrylamide gels were quantified by scanning laser densitometry.

EXAMPLE 1

Subcellular Fractionation and Solubilization of Clipsin

In pilot studies, we identified clipsin using enzymographic gels as a $M_r$ 25,000 proteolytic activity present in 1-week-old but not adult rat brain; consequently, we used the former source in further characterization of the protease. Clipsin was detected only in particulate fractions of rat brain after ultracentrifugation, and it proved to be completely resistant to solubilization by treatment of membranes with detergents (1% Triton X-100 or 1% CHAPS) or a low ionic strength buffer. These treatments were therefore used to increase the specific activity of the protease and to remove other activities. The gelatinolytic activity of clipsin detected by enzymography increased with successive membrane treatments. Because gelatin, a general protease substrate used in this type of assay, is unlikely to be a preferred clipsin substrate, this observation most likely indicates that the polyacrylamide-bound $^{125}I$-labeled gelatin competes with co-migrating proteins in the less enriched fractions as substrates for clipsin.

In the presence of 5 mM $Ca^{2+}$, clipsin activity was partially inhibited, and a number of higher molecular weight protease activities were revealed. These activities, which represent a family of $Ca^{2+}$-dependent brain metalloproteases described previously (Nelson et al., (1989) *J. Neurochem.* 53, 641-647), were largely removed by the membrane extraction steps. The relative enrichment of clipsin activity versus total protein is illustrated by Coomassie Blue protein stains of the various protease-containing fractions. Although the enzymographic technique is only linear over a restricted range, it appears that greater than 50% of clipsin can be solubilized by a 30-min treatment of the low ionic strength-extracted membrane preparation with 1M $MgCl_2$. Attempts to extract a greater percentage of activity by increasing the extraction temperature resulted in an overall decrease in activity. After pelleting out membranes by centrifugation, the supernatant from this $Mg^{2+}$ extraction was dialyzed against $Mg^{2+}$ extract buffer, as described above, and used for subsequent in vitro experiments.

EXAMPLE 2

Inhibitor Profile of Clipsin

Clipsin was initially characterized using enzymographic gels to distinguish it from any other protease activities potentially present in the $Mg^{2+}$ extract. Because clipsin showed no dependence on $Ca^{2+}$, and traces of $Ca^{2+}$-dependent metalloprotease activity were detectable in the $Mg^{2+}$ extract, clipsin activity was routinely assayed in the presence of 1 mM EDTA. No other proteases were detectable in $Mg^{2+}$ extract under these conditions. As demonstrated previously, the brain metalloproteases are completely dependent on $Ca^{2+}$ for activity (Nelson et al., (1989) *J. Neurochem.* 53, 641-647). Although clipsin showed some inhibition by $Ca^{2+}$ at 5 mM concentrations, it showed little or no inhibition by several divalent cations, including $Ca^{2+}$, $Mg^{2+}$, $Zn^{2+}$, and $Mn^{2+}$ at 1 mM concentrations. Lack of complete inhibition by mM $Zn^{2+}$ or by 1,10-0-phenanthroline indicated further that clipsin was not one of the previously reported brain metalloproteases (Nelson et al., (1989) *J. Neurochem.* 53, 641-647). Clipsin was not active at low pH, nor was it inhibited by pepstatin, suggesting that it was not an aspartic protease. Clipsin was also not inhibited by iodoacetic acid or N-ethylmaleimide, agents specific for cysteine proteases. Only phenylmethylsulfonyl fluoride and diisopropyl fluorophosphate inhibited clipsin activity, indicating its probable identity as a serine protease. Although these two inhibitors have a broad specificity for serine proteases, they both bind relatively slowly, accounting for the partial activity of clipsin remaining on the gels.

A group of synthetic peptide boronic acids was next tested as potential inhibitors of clipsin. These peptide inhibitors, which have been described previously (Kettner et al., (1984) *J. Biol. Chem.* 259, 15106-15114; U.S. Pat. No. 4,499,082, issued Feb. 12, 1985 to Kettner and Shenvi), rapidly inhibit different subtypes of serine proteases depending on the target amino acid at the P1 position of the peptide. We found that clipsin was preferentially inhibited by MeO-Suc-Ala-Ala-Pro-boro-Phe-OH (MeO-, methoxy; Suc, succinyl; boro, (R)-acetamido-2-phenylethane boronic acid, where R is the L-amino acid preceded by the prefix "boro"), an inhibitor specific for chymotrypsin-like enzymes, but not by MeO-Suc-Ala-Ala-Pro-boro-Ala-OH and MeO-Suc-Ala-Ala-Pro-boro-Val-OH, inhibitors of leukocyte and pancreatic elastase, respectively, and only marginally by Bz-Pro-Phe-boro-Arg-OH (Bz-, benzyl), an inhibitor of trypsin-like serine proteases (European Patent Application Number 88108817.3, to Kettner and Shenvi, published Dec. 7, 1988). Based on this characterization, we established an in vitro assay of $Mg^{2+}$ extract using Suc-Ala-Ala-Pro-Phe-p-nitroanilide, a chromogenic substrate selective for chymotrypsin-like proteases. $Mg^{2+}$ extract contained activity capable of hydrolyzing the chromogenic substrate, suggesting the presence of an active form of clipsin in vitro and indicating low or nonexistent levels of potential endogenous clipsin inhibitors in $Mg^{2+}$ extract. We therefore measured the ability of the various peptide boronic acids to inhibit Suc-Ala-Ala-Pro-Phe-p-nitroanilide hydrolysis by $Mg2+$ extract in vitro and compared it with the inhibition of clipsin activity seen on the enzymographs. The two methods yielded identical inhibitory profiles, further suggesting that the Suc-Ala-Ala-Pro-Phe-p-nitroanilide-hydrolyzing activity in $Mg^{2+}$ extract was due to clipsin as identified on enzymographs.

TABLE 1

| Sample # | Relative Clipsin Activity |
|---|---|
| 1 | 100 |
| 2 | 8 |
| 3 | 97 |
| 4 | 94 |
| 5 | 84 |

Effects of peptide boronic acids on clipsin activity measured in vitro and by enzymography. $Mg^{2+}$ extract was separated on substrate-containing gels (10% polyacrylamide) and tested for activity in the presence of various peptide boronic acid serine protease inhibitors (10 μM final concentrations). Parallel samples of $Mg^{2+}$ extract were tested for inhibition of chymotrypsin-like activity against Suc-Ala-Ala-Pro-Phe-p-nitroanilide in vitro. In the in vitro assay, $Mg^{2+}$ extract at 20% final (or 1.4 nM clipsin) was preincubated for 10 min at 37° C. with one of the peptide boronic acids (10 μM final concentration) in $Mg^{2+}$ extract buffer prior to addition of 2 mM Suc-Ala-Ala-Pro-Phe-p-nitroanilide for 1 h at 37° C. The reaction was terminated with 200 μg/mL soybean trypsin inhibitor. The values generated represent change in absorbance ($\Delta OD$) as a percentage of the control value (100%) and are listed at the bottom of the corresponding panel from the enzymographic analysis. Sample 1, control (addition of $Mg^{2+}$ extract buffer alone); Sample 2, MeO-Suc-Ala-Ala-Pro-boro-Phe-OH; Sample 3, MeO-Suc-Ala-Ala-Pro-boro-Ala-OH; Sample 4, MeO-Suc-Ala-Ala-Pro-boro-Val-OH; and Sample 5, Bz-Pro-Phe-boro-Arg-OH. Enzymographic analysis was performed twice. The in vitro values are the average of three determinations.

EXAMPLE 3

Binding of α-1-AChy to Clipsin

α-1-AChy is an irreversible inhibitor of chymotrypsin-like proteases (Travis et al., (1978) *Biochemistry* 17, 5651-5656). Moreover, α-1-AChy immunoreactivity and mRNA have been reported in brain (Justice et al., (1987) *J. Cell Biochem.* 34, 227-238; Abraham et al., (1988) *Cell* 52, 487-501; Abraham et al., (1990) *Neurobiol. Aging, in press*), making α-1-AChy a potential endogenous inhibitor of clipsin. We therefore pursued the characterization of clipsin as a chymotrypsin-like protease by determining whether α-1AChy could irreversibly inhibit clipsin. Pilot experiments determined that α-1-AChy was an effective inhibitor of clipsin activity in vitro (using Suc-Ala-Ala-Pro-Phe-p-nitroanilide as substrate). To determine the time course of this inhibition, we first constructed titration curves of percent residual clipsin activity versus α-1-AChy concentration measured after various preincubation times. Each of the plots was linear and yielded an extrapolated titration point of clipsin activity. These titration points were plotted against preincubation time. The plot showed that the titration of clipsin with α-1-AChy became asymptotic between 60 and 120 min of preincubation. The titration curve at 120 min yielded a value of 1.4 nM α-1-AChy necessary to inhibit 100% clipsin activity. Assuming a 1:1 stoichiometry for α-1-AChy binding to clipsin (based on previously determined α-1-AChy-binding stoichiometries with chymotrypsin and cathepsin G; Travis et al., (1978) *Biochemistry* 17, 5651-5656) and a molecular weight of 25,000 kDa for clipsin, this indicates a 35 ng/mL concentration of clipsin/total $Mg^{2+}$ extract protein concentration of 200 μg/mL. To determine whether clipsin was similar to other chymotrypsin-like enzymes in forming sodium dodecyl sulfate-resistant bonds with α-1-AChy, we used the enzymographic assay. After separation of proteins on the gelatin-containing polyacrylamide gels, protease activity was allowed to continue to exhaustion (out of the linear range of the assay) to enhance differences between samples close to the titration point of clipsin. Clipsin activity disappeared from the gels between 0.9 and 1.5 nM added α-1-AChy, indicating (a) that α-1-AChy formed complexes with clipsin which survived exposure to sodium dodecyl sulfate; and (b) that the concentration range in which α-1-AChy bound to all free clipsin in the $Mg^{2+}$ extract fraction agreed with the titration point calculated from the in vitro assay.

To standardize our estimates of enzyme concentration for kinetic studies, we also used α-1-AChy to titrate the activity in commercial preparations of human cathepsin G and bovine chymotrypsin. Chymotrypsin was titrated at 100-fold higher concentrations of enzyme and inhibitor due to its relatively low rate of association with α-1-AChy (Beatty et al., (1980) *J. Biol. Chem.* 255, 3931-3934). On this basis, cathepsin G and chymotrypsin contained 88% and 96%, respectively, of their theoretical activities. Such values are reasonable assuming less than 100% active protease and/or the presence of impurities in the preparations. The kinetic values generated in Table 2 reflect adjustments in enzyme concentration based on titrated values.

TABLE 2

| Protease | Substrate (R:Suc—Ala—Ala—Pro) (R': MeO—Suc—Ala—Ala—Pro) | Substrate concentration range mM | $K_m$ mM | $k_{cat}$ $s^{-1}$ | $k_{cat}/K_m$ $M^{-1}s^{-1}$ |
|---|---|---|---|---|---|
| Clipsin | R—Phe-p-nitroanilide | 0.1-2.0 | 0.82 | 47 | 57,000 |
| | R'—Met-p-nitroanilide | 0.1-2.0 | 0.21 | 1.1 | 5,200 |
| Cathepsin G | R—Phe-p-nitroanilide | 0.1-2.0 | 3.3 | 16 | 4,800 |
| | R'—Met-p-nitroanilide | 0.1-1.0 | 0.54 | 2.3 | 4,300 |
| Chymotrypsin | R—Phe-p-nitroanilide | 0.02-2.0 | 0.13 | 120 | 910,000 |
| | R'—Met-p-nitroanilide | 0.2-2.0 | 1.8 | 80 | 44,000 |

Kinetic constants for the hydrolysis of tetrapeptide p-nitroanilide substrates by rat brain clipsin, human leukocyte cathepsin G, and bovine chymotrypsin are shown in Table 2. The kinetic constants were determined in 50 mM Hepes (pH 7.5), 1 mM EDTA, 0.5M NaCl, 0.1% Brij 35, and 10% dimethyl sulfoxide at 50° C. $K_m$ values were determined by the method of Lineweaver and Burk. $k_{cat}$ values were calculated using α-1-AChy-titrated values for total enzyme concentration. Kinetic values are an average drawn from three Lineweaver-Burk plot determinations.

Using the titrated value for clipsin concentration in the $Mg^{2+}$ extract, we combined equimolar concentrations of clipsin and α-1-AChy to determine the association rate constant between these two proteins, as described previously (Equation 4 in Beatty et al., (1980) *J. Biol. Chem.* 255, 3931–3934). The $k_{assoc}$ was determined to be $2.9 \times 10^6 M^{-1} s^{-1}$, a value falling between those determined previously for chymotrypsin and cathepsin G (Beatty et al., (1980) *J. Biol. Chem.* 255, 3931–3934).

EXAMPLE 4

Kinetics of Substrate Hydrolysis by Clipsin Versus Other Chymotrypsin-like Proteases We tested the ability of clipsin to hydrolyze several other peptide-nitroanilide substrates, including Suc-Ala-Ala-Pro-Leu-p-nitroanilide, MeO-Suc-Ala-Ala-Pro-Val-p-nitroanilide, Bz-Arg-p-nitroanilide, and MeO-Suc-Ala-Ala-Pro-Met-p-nitroanilide. We found detectable hydrolysis only with the last substrate, which is also a substrate for chymotrypsin-like proteases (Nakajima et al., (1979) *J. Biol. Chem.* 254, 4027–4032). We therefore used both MeO-Suc-Ala-Ala-Pro-Met-p-nitroanilide and Suc-Ala-Ala-Pro-Phe-p-nitroanilide to do a kinetic comparison of clipsin versus bovine chymotrypsin and human leukocyte cathepsin G. As shown above in Table 2, clipsin could be distinguished kinetically from both cathepsin G and chymotrypsin. Clipsin was similar to cathepsin G in having a greater affinity for the methionine-containing versus the phenylalanine-containing nitroanilide substrate and in having a similar catalytic efficiency to cathepsin G against the methionine-containing substrate. In contrast to cathepsin G, however, clipsin was 11-fold more catalytically efficient against the phenylalanine-containing p-nitroanilide substrate. Chymotrypsin kinetic constants were also distinct from clipsin in that chymotrypsin had a lower $K_m$ for the phenylalanine-than the methionine-containing substrate and had $k_{cat}/K_m$ values for these substrates 16- and 8.5-fold higher, respectively than those determined for clipsin.

EXAMPLE 5

Preferential Hydrolysis of Brain β-APP by Clipsin

We began looking for potential endogenous substrates of clipsin by incubating rat cortical membranes with $Mg^{2+}$ extract and measuring loss of the major protein bands following separation of the incubated samples by polyacrylamide gel electrophoresis. One protein doublet out of 20 bands measured showed a 66% decrease following incubation with the clipsin-containing extract. This decrease could be blocked by inclusion of the clipsin inhibitor MeO-Suc-Ala-Ala-Pro-boro-Phe-OH but not the elastase inhibitor MeO-Suc-Ala-Ala-Pro-boro-Val-OH. No other bands varied more than 25%, and no protease activity endogenous to cortical membranes could be detected when comparing 37° C. incubated membranes with parallel samples kept on ice.

Because the generation of β-amyloid from brain β-APP suggests a cleavage event characteristic of a chymotrypsin-like enzyme (Kang et al., (1987) *Nature* 325, 733–736; Abraham et at., (1988) *Cell* 52, 487–501), we immuno-stained Western blots of these same test samples for β-APP using a polyclonal antiserum raised against a synthetic peptide corresponding to residues 676–695 of the β-APP carboxyl terminus. The clipsin-containing extract caused a 90% loss of β-APP immunoreactivity, and this loss was specifically blocked by the clipsin inhibitor MeO-Suc-Ala-Ala-Pro-boro-Phe-OH.

EXAMPLE 6

Ontogeny and Tissue Distribution of Clipsin

To determine the developmental period during which clipsin activity was highest in brain, we prepared in parallel $Mg^{2+}$ extracts from forebrain of rats at different postnatal ages. We found the peak of clipsin activity to occur at around postnatal day 5. No activity was found in alternate fractions generated during the preparation of $Mg^{2+}$ extract, arguing against an altered compartmentalization of clipsin during development. To quantify these changes in activity, the $Mg^{2+}$+extract fractions from different aged brains were also assayed for Suc-Ala-Ala-Pro-Phe-p-nitroanilide hydrolysis in vitro. The in vitro values corresponded well to the enzymographic detection of clipsin activity and indicate that clipsin activity is very low in newborn and adult rat brain but experiences a dramatic 12–14-fold increase during the first 2 weeks after birth.

We also examined the distribution of activities similar to clipsin among different tissues to compare with what has been reported for other chymotrypsin-like proteases. Because many chymotrypsin-like proteases have apparent migration rates centering around $M_r$ 25,000 (Barrett et al., (1980) *Mammalian Proteases, Vol.* 1, *Enzymol.* 80, 1–919) prepared $Mg^{2+}$ extracts from each tissue tested to select for proteases similar to clipsin with regard to solubilization properties and lower. Both 5-day-old and adult rat spleen were highest in an activity migrating close to clipsin's apparent molecular weight. Adult lung showed a dramatic developmental increase in a similar sized protease from 5-day-old to adult. Brain was distinguished as the only tissue having an $M_r$ 25,000 activity that was more highly expressed at day 5 than in adult.

Although the enzymographic assay normally separates proteases from endogenous inhibitors prior to measuring their activity, this procedure does not dissociate sodium dodecyl sulfate-resistant protease/protease inhibitor complexes, such as were demonstrated to occur in the present report between clipsin and α-1-AChy. Potentially, then, the decrease in clipsin activity in brain after day 5 might not represent a decrease in clipsin expression but rather an increase in α-1-AChy levels and/or an increased access of α-1-AChy to clipsin. Such questions may be addressed using antibodies and nucleotide probes raised against both clipsin and α-1-AChy.

The unusual ontogeny of clipsin activity in brain suggests that clipsin has a very circumscribed role that is largely constrained to a brief developmental period. It is expected that inappropriate expression of clipsin activity outside this developmental period, for example, in response to brain injury, might lead to inappropriate processing of clipsin substrates such as β-APP which in turn may form neurite plaques. In particular, it is expected that clipsin could generate the amino terminus of β-amyloid.

Although clipsin was examined in rats, we expect a similar enzyme to be present in human brain, with similar properties. Futher, we expect to be able to obtain an antibody specific to clipsin, to make recombinant clipsin, and to prepare purified clipsin. Clipsin in substantially pure form appears to enable screening of compounds for usefulness in treating neuropathologies such as Down's syndrome and Alzheimer's disease. These compounds will be tested for their ability to inhibit clipsin.

It is expected that one can determine the amino acid sequence or partial amino acid sequence, or use antibody reagents, to isolate the gene or cDNA encoding clipsin. The cDNA clones can be used to express recombinant clipsin. Standard techniques would be used to accomplish the above.

It should be understood, however, that the foregoing description of the invention is intended merely to be illustrative thereof and other modifications, embodiments, and equalivents may be apparent to those skilled in the art without departing from its spirit.

Having thus described the invention what we desire to claim and secure by Letters Patent is:

1. A method of evaluating compounds for an ability to inhibit protease activity of a selected protein, comprising:

(a) providing in a container a solution containing: a known quantity of said selected protein; a known quantity of a peptide substrate comprising a cleavage site for said selected protein wherein said cleavage site comprises an amino acid selected from the group consisting of tyrosine, tryptophan, phenylalanine, methionine and leucine; and a known quantity of a compound to be evaluated as an inhibitor of the protease activity of said selected protein under conditions which permit the cleaving of said cleavage site by said selected protein and which permit the binding of the compound to said selected protein;

wherein said protease activity of said selected protein is exhibited by the cleavage of said cleavage site on the carboxyl side of said amino acid;

wherein said selected protein has an apparent molecular weight of between 23,800 and 26,200 daltons as measured by polyacrylamide gel electrophoresis in the presence of sodium dodecyl sulfate, is capable of binding with α-1-antichymotrypsin in a sodium dodecyl sulfate-resistant manner, is capable of extraction from the particulate fraction of a homogenate of a rat brain, and said protease activity of said selected protein is capable of being inhibited by the serine protease inhibitor phenylmethylsulfonyl fluoride, and where said selected protein is capable of proteolysis of a β-amyloid percursor protein;

(b) incubating the selected protein, the peptide substrate containing said cleavage site and the compound to be evaluated; and (c) measuring the extent to which the compound to be evaluated inhibits said protease activity of said protein.

2. The method of claim 1 in which said selected protein is extractable by contacting the particulate fraction with a solution containing about 1M of a magnesium salt.

3. The method of claim 2 in which said selected protein further includes the property of being resistant to solubilization from association with the particulate fraction by a solution of 1 mM N-2-hydroxyethylpiperazine-N'-2-ethanesulfonic acid (Hepes), pH 7.5 and 0.1 mM ethylenediaminetetraacetic acid (EDTA).

4. The method of claim 3 in which said selected protein further includes the property of being resistant to solubilization from association with the particulate fraction by 1% polyoxyethylene ether surfactant or 30 ((3-cholamidopropyl)-dimethylammonio)-1-propanesulfonic acid (CHAPS).

5. The method of claim 1 wherein the selected protein has an apparent molecular weight of about 25,000 daltons as measured by polyacrylamide gel electrophoresis in the presence of sodium dodecyl sulfate.

* * * * *